United States Patent [19]

Shimatani et al.

[11] Patent Number: 5,180,059
[45] Date of Patent: Jan. 19, 1993

[54] PACKAGE OF SANITARY TAMPON

[76] Inventors: Sumie Shimatani; Kazuo Shimatani, both of 109-3 Koyato, Kouza-gun, Kanagawa, Japan

[21] Appl. No.: 598,623

[22] PCT Filed: Apr. 11, 1989

[86] PCT No.: PCT/JP89/00385
§ 371 Date: Oct. 17, 1990
§ 102(e) Date: Oct. 17, 1990

[87] PCT Pub. No.: WO91/04856
PCT Pub. Date: Apr. 18, 1991

[30] Foreign Application Priority Data

Apr. 12, 1988 [JP] Japan .................................. 63-48867

[51] Int. Cl.⁵ .................................................. B65D 17/06
[52] U.S. Cl. .................................. 206/440; 206/438; 206/495; 206/529; 604/904
[58] Field of Search .............. 206/438, 440, 492, 495, 206/529; 604/385.1, 386, 393, 904

[56] References Cited

U.S. PATENT DOCUMENTS

| | | | |
|---|---|---|---|
| 2,319,560 | 5/1943 | Salfisberg | 206/492 |
| 2,968,396 | 1/1961 | Pratt | 206/440 |
| 3,017,990 | 1/1962 | Singerman | 206/440 |
| 3,058,469 | 10/1962 | Crockford | 604/904 |
| 3,062,371 | 11/1962 | Patience | 206/440 |
| 3,119,495 | 1/1964 | Pratt | 206/440 |
| 3,344,915 | 10/1967 | Rawlings | 206/440 |
| 3,358,686 | 12/1967 | Asaka | 206/438 |
| 3,652,006 | 3/1972 | Trewella | 206/440 |
| 3,674,029 | 7/1972 | Bates et al. | 604/904 |
| 3,698,549 | 10/1972 | Glassman | 206/440 |
| 3,946,737 | 3/1976 | Kobler | 604/385.1 |
| 4,211,225 | 7/1980 | Sibalis | 604/385.1 |
| 4,286,639 | 9/1981 | Murphy | 206/440 |
| 4,553,965 | 11/1985 | Conn et al. | 604/904 |
| 4,556,146 | 12/1985 | Swanson et al. | 206/440 |
| 4,743,237 | 5/1988 | Sweere | 604/904 |
| 4,917,675 | 4/1990 | Taylor et al. | 604/385.1 |

FOREIGN PATENT DOCUMENTS 414453 12/1966 Switzerland .................... 206/440

Primary Examiner—David T. Fidei
Attorney, Agent, or Firm—Edwin E. Greigg; Ronald E. Greigg

[57] ABSTRACT

A package of a sanitary tampon used to absorb menstrual blood, the package comprising a packing sheet assembly composed of two sheets superposed one upon another to form sheet parts that extend in at least Three directions, two of the sheet parts being bonded at their sides facing each other and at a free end so as to enclose one part of the tampon, the other sheet part enclosing the other part of the tampon in such a state that when the thus packed tampon is used a periphery of the tampon's lower part held with the fingers is insulated from a periphery of the tampon's upper part to be inserted in the vagina thus protecting the fingers from any smudge.

3 Claims, 3 Drawing Sheets

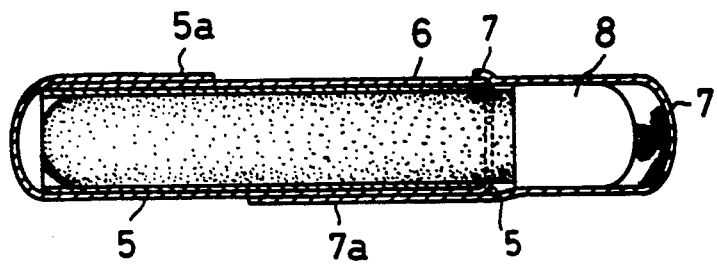
FIG. 3
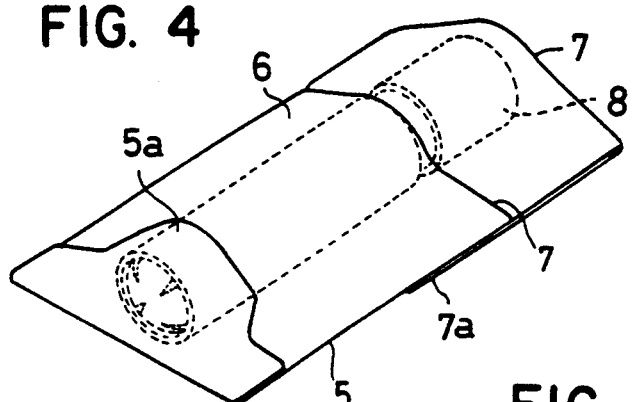
FIG. 4
FIG. 5
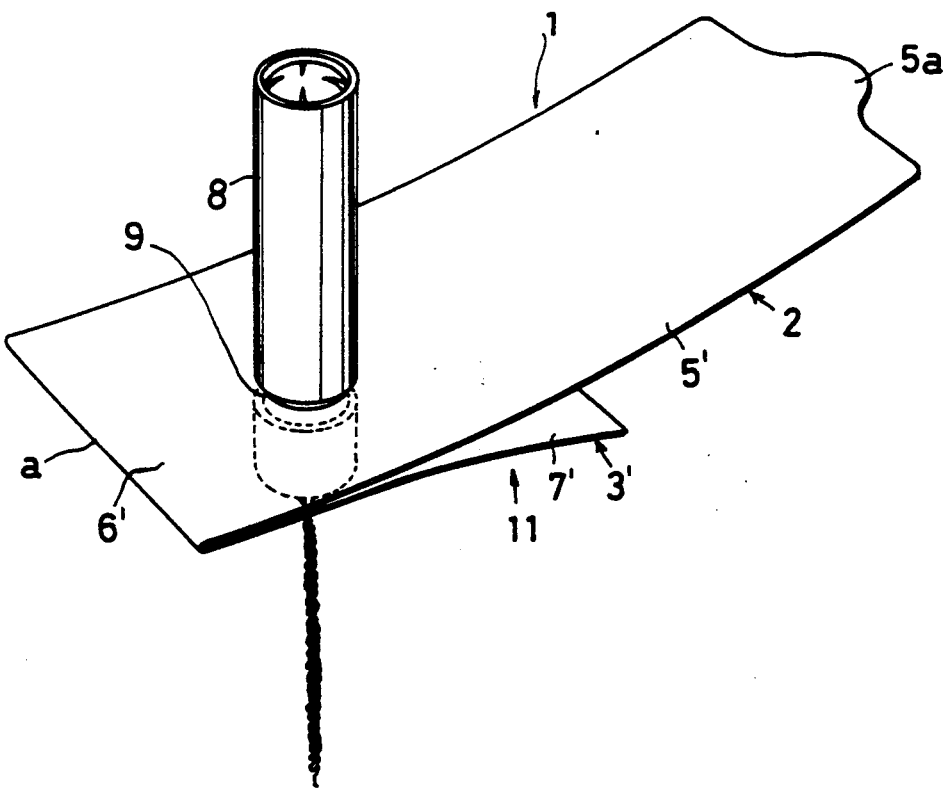

PACKAGE OF SANITARY TAMPON

FIELD OF THE INVENTION

The present invention relates to a package of sanitary tampon capable of protecting fingers from smudge when a sanitary tampon is inserted.

BACKGROUND OF THE INVENTION

The sanitary tampons are individually packed one in one package so that they may be carried in a hygienic state prior to use thereof.

There have been used such packages that are cylindrical bags in their shape and adapted to seal up the sanitary tampons, in spite of a variety in their materials.

Such conventional cylindrical packages serve only the function of sealing up of the sanitary tampons, that is, they are merely thrown away giving no additional use once they are opened.

In view of this point, it is an object of the invention to provide a package of sanitary tampon that has an additional function useful for the users of sanitary tampons even after it is opened.

SUMMARY OF THE INVENTION

In order to achieve the aforesaid object, the present invention employs technical features in a structure described below.

The structure comprises a packing sheet assembly composed of two sheets that are superposed one upon another to form at least three sheet parts, these sheet parts thereby extending respectively in three directions, any two of said three sheet parts folded down at a suitable position such that areas of an inner surface of the thus folded sheet parts face each other, further comprises a sanitary tampon having one longitudinal part put through an opening, the opening formed through the sheet parts at a location near the suitable position, said two sheet parts being separably bonded together at their sides that face each other and also at a free end to thereby enclose the longitudinal part of the sanitary tampon, wherein the remaining one of said three sheet parts also is folded down to enclose the other longitudinal part of the sanitary tampon, said remaining sheet parts separably adhering at its two sides and free end to an outer surface of one of the aforesaid two sheet parts mentioned above.

Such a packed sanitary tampon is used by separating the sheet parts from each other at their adhering portions, thus causing said sheet parts to take their positions perpendicular to each other. A lower portion of the sanitary tampon is then held by the fingers in such a state that the sheet parts cover upper portions of the fingers. Subsequently, an upper portion of the sanitary tampon is pushed through a mouth of the vagina so that the tampon as a whole is then inserted in the vagina. Because the sheet parts are positioned above the fingers when the sanitary tampon is inserted, the fingers do not come in a direct contact with the mouth of the vagina whereby a hygienic insertion of the tampon is ensured.

According to the invention, the sheet parts intervene between the periphery of the lower portion of the sanitary tampon that is held with the fingers when inserted after unsealing of the package and the periphery of the upper portion already inserted in the vagina, as apparent from the foregoing description. Therefore, the fingers are protected from menstrual blood even if it flows down along the the upper portion of the tampon.

BRIEF DESCRIPTION OF THE DRAWINGS

FIG. 3 is a cross section taken along a line III—III in FIG. 2;

FIG. 4 is a perspective view of the package in its closed state;

FIG. 5 is a cross sectional view and FIG. 6 is a perspective view in an opened state of an another package in a further embodiment, respectively.

DETAILED DESCRIPTION OF THE PREFERRED EMBODIMENTS

Figure 1:
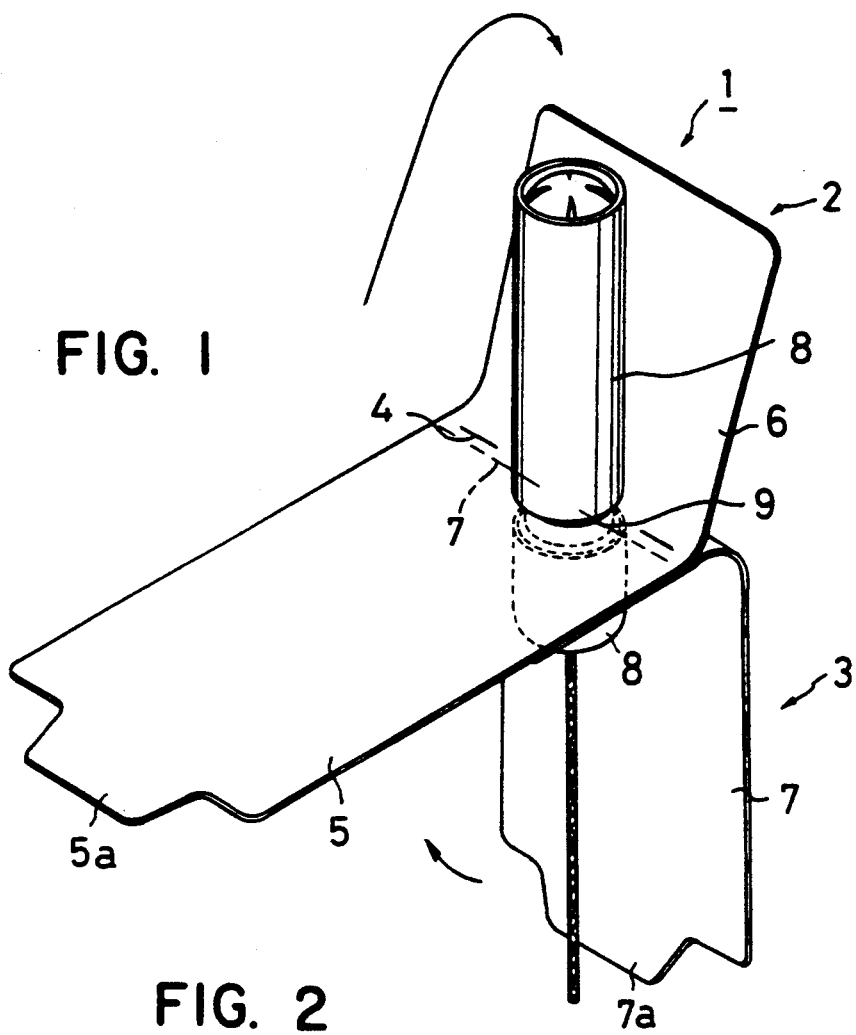
FIG. 1 is a perspective view of the a package of sanitary tampon in its opened state according to an embodiment of the invention.

The present invention will be explained in more detail based on the embodiments shown in the drawings.

Figure 2:
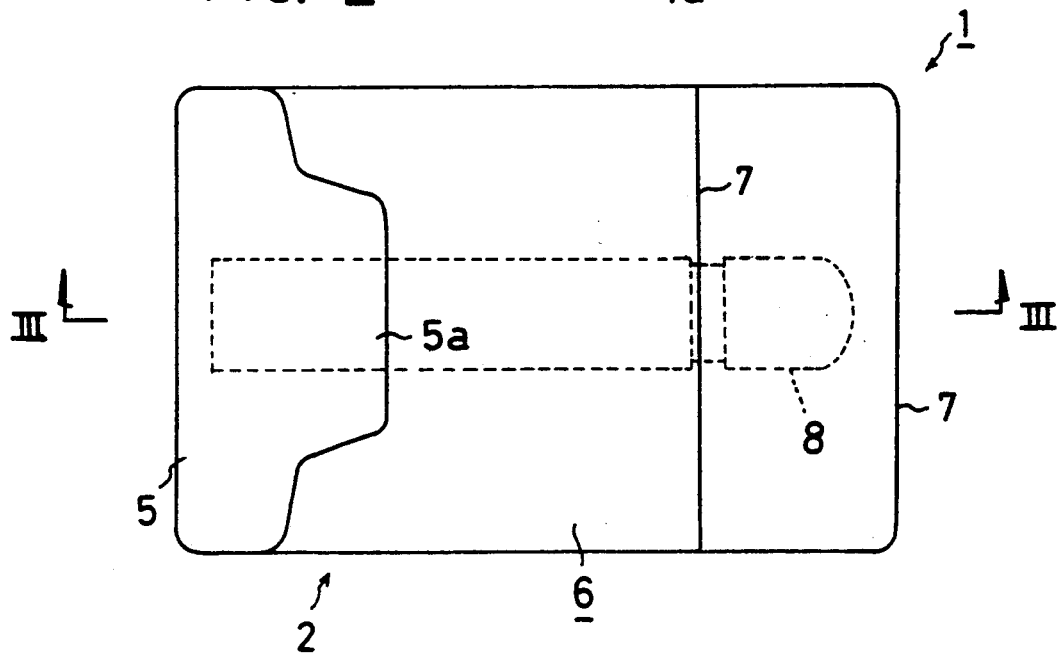
FIG. 2 is a plan view of the package in its closed state.

A package 1 illustrated in FIGS. 1 to 4 as an embodiment of the invention is of a shape similar to a postal rectangular envelope, as seen in the plan view of FIG. 2, a cross sectional view in FIG. 3 and in the perspective view of FIG. 4.

The numerals 2 and 3 denote rectangular sheets that compose the package 1 and are of the same width. One of the rectangular sheets is 2 longer a little than the other 3. The longer sheet 2 is bent at a line 4 corresponding to about one third of its transverse length. Bonded to an outer surface of this line 4 is the shorter sheet 3 so that these sheets 2 and 3 form three sheet parts 5, 6 and 7 which extend in three directions, respectively.

The first sheet part 5 and the second sheet part 6 originate from the sheet 2 and are bent at that line 4 referred to above with the sheets facing each other so as to be bonded to each other at their sides facing one another with an adhesive which allows separation of the bonded members. The sheet part 5 has a tab 5a formed at a protruding extreme remote end from the bonded area. The tab 5a is for separable (peelable) adhesion onto an outer surface of the second sheet part 6.

An opening 9 for insertion of a sanitary tampon 8 therethrough is formed at the bent portion 4. One longitudinal part ( an upper portion ) of the sanitary tampon 8 is put through the opening 9 so that it is received in a bag-like receptacle sealed up with the first and second sheet parts 5 and 6.

The other part ( a lower portion ) of the sanitary tampon 8 protrudes outwardly from the opening 9 is enclosed in its longitudinal direction by the third sheet part 7 that is folded down in a direction opposite the direction in which the the first sheet part 5 is folded down. The third sheet part 7 also is provided with a tab 7a in such a state that the tag 7a is separably bonded along with the sides of said sheet part 7 to an outer surface of the first sheet part 5.

Therefore, the package 1 constructed in this manner will assume an appearance as shown in FIG. 1 if the tab 1a of the first sheet part 5 as well as the tab 7a of the third sheet part 7 are pulled one after another to separate the first sheet part 5 from the second one 6 and to separate the third sheet part 7 from the first one 5.

In this state of the package, a user may hold the sheets with her hand positioned under the lower surfaces ( in a sense of the drawings ) of the first and third sheet parts 5 and 7, and may grip its lower portion of the sanitary tampon 8 between her middle finger and forefinger. Thus, her fingers do not touch her body near the vagina, and will be protected from her menstrual blood even if it flows down along the sanitary tampon 8.

More than two sheets may be employed in the package according to the invention as far as they are bonded to each other at their ends such that they may individually form one of three sheet parts extending in three different directions.

Figure 6:
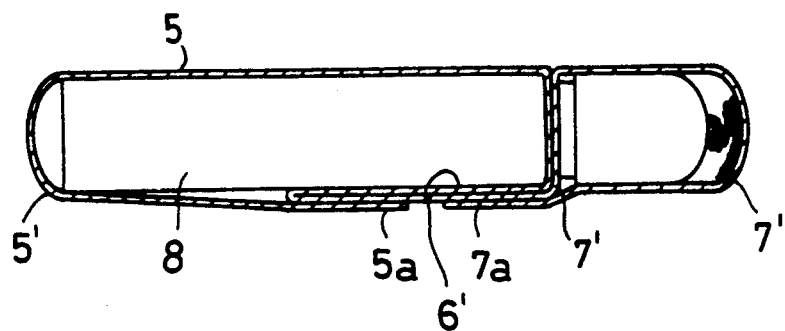

FIGS. 5 and 6 show another embodiment wherein a long sheet 11 is folded down at its bent portion (a) to form a longer upper sheet section 2' as well as a shorter lower sheet section 3', in a doubled up state. An opening 9 is formed near the bent portion (a) for insertion of the sanitary tampon 8. The doubled sheet part 6' is positioned along an upper portion of the tampon, as shown in FIG. 6, and a long upper sheet part 5' located on the other side is then folded around the upper end of said tampon 8 so that it may be bonded to the doubled sheet part 6'. A shorter sheet part 7' is folded over the lower end of said sanitary tampon 8 and bonded also to the doubled sheet part 6'.

The long sheet part 5' may be overlaid on or alternately positioned below the shorter sheet part 7' to adhere thereto. The doubled sheet part 6' may be such that its component parts are bonded to each other.

Figure 7:
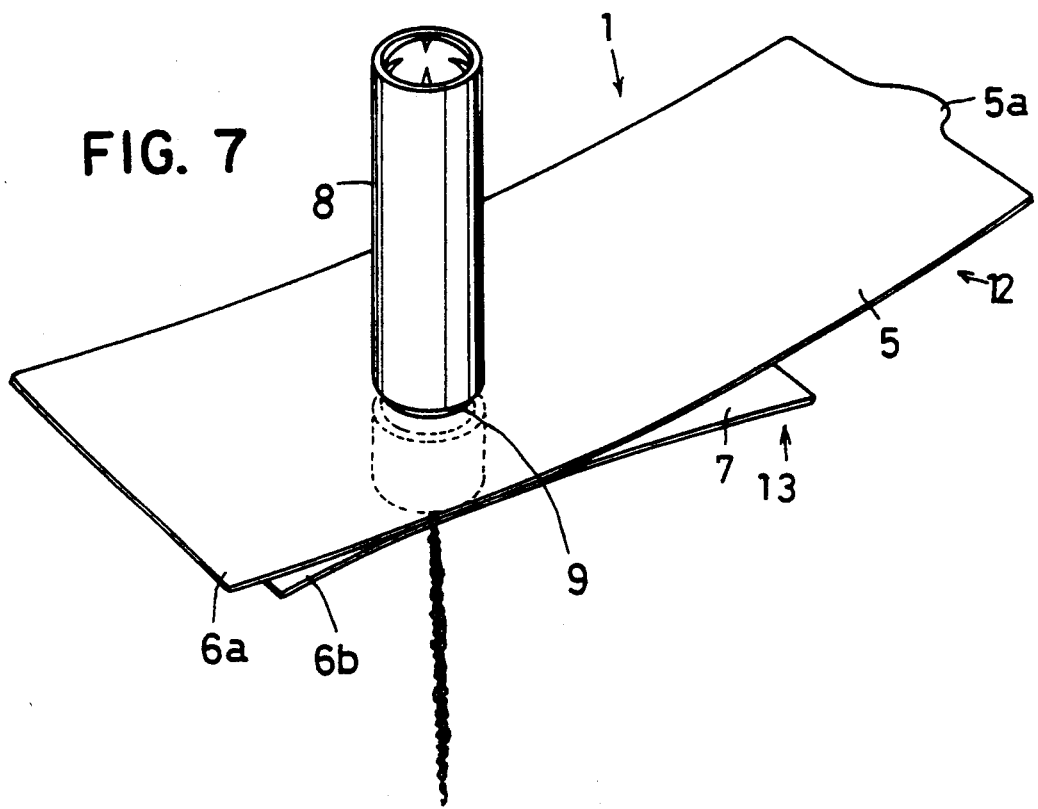
FIGS. 7 and 8 also are cross sectional view and a perspective view in opened state, of a still another package in a still further embodiment, respectively.
Figure 8:
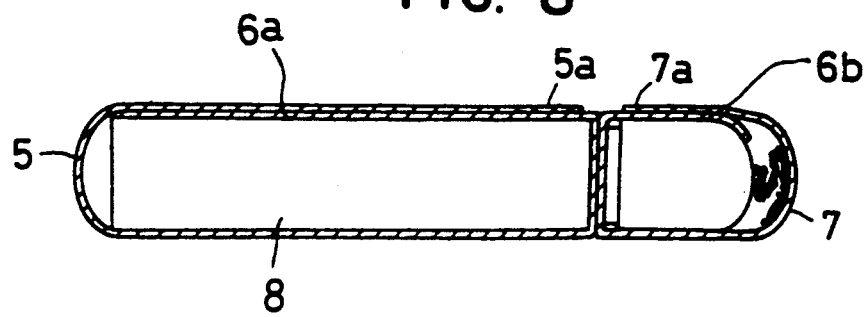

FIGS. 7 and 8 illustrate a still another embodiment in which a longer sheet 12 is used together with a shorter sheet 13. A sanitary tampon 8 is inserted through an opening 9 formed at a location near a middle portion of these sheets. The sheet parts 5 and 6a respectively extending leftwards and rightwards in the drawings as shown in FIG. 8 are bonded to each other to enclose an upper part of the sanitary tampon 8. The sheet parts 6b and 7 respectively extending leftwards and rightwards also are bonded to each other to enclose a lower part of the tampon 8 as shown in a cross sectional view in FIG. 8.

The invention may be embodied in such manners as described hereinbefore.

What is claimed is:

1. A package of a sanitary tampon comprising a packing sheet assembly composed of at least one sheet having three sheet parts that are superimposed one upon another to form said package, two of the three sheet parts are folded along a line perpendicular to their edges at a suitable position such that areas of an inner surface of the thus folded two sheet parts face each other, at least one of said sheet parts includes an aperture juxtaposed said folded line, a sanitary tampon having first and second longitudinal parts with said second longitudinal part extending through said aperture formed through the at least one sheet part at a location near the aforesaid suitable position, said two sheet parts that face each other being separably bonded to each other along their facing edges and also at a free end of one of said two sheets to thereby enclose said first longitudinal part of the sanitary tampon, wherein the remaining one of said three sheet parts is folded to enclose the second longitudinal part of the sanitary tampon, said remaining sheet part being separably adhered at its two sides and a free end to an outer surface of one of the aforesaid two sheet parts.

2. A package of a sanitary tampon in accordance with claim 1 wherein the packing sheet assembly comprises first and second sheets, said first sheet encompasses said first longitudinal part of said tampon and the second sheet is bonded to the first sheet near a middle portion thereof an dhaving almost the same width as the first sheet and encompassing the second longitudinal portion fos aid tampon.

3. A package of a sanitary tampon in accordance with claim 1 wherein the packing sheet assembly comprises first and second sheets bonded to each other and having almost the same width, said sheets are bonded together to form first, second and third sheet parts which extend in different directions relative to a longitudinal plane with one of said sheets lying along said longitudinal plane, said first and second sheet parts are folded facing each other and sealed along their edges to encompass said first longitudinal portion of said tampon, and said third sheet part is folded upon itself and sealed along facing edges to encompass said second longitudeinal portion of said tampon.

* * * * *